United States Patent
DiMatteo et al.

(10) Patent No.: US 7,753,907 B2
(45) Date of Patent: Jul. 13, 2010

(54) MEDICAL DEVICE SYSTEMS AND METHODS

(75) Inventors: Kristian DiMatteo, Waltham, MA (US); William J. Shaw, Cambridge, MA (US); Robert F. Rioux, Ashland, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 585 days.

(21) Appl. No.: 10/977,255

(22) Filed: Oct. 29, 2004

(65) Prior Publication Data

US 2005/0070888 A1 Mar. 31, 2005

(51) Int. Cl.
*A61B 18/18* (2006.01)
*A61B 17/22* (2006.01)
(52) U.S. Cl. ........................... 606/41; 606/159
(58) Field of Classification Search ............ 606/41, 606/42, 48–50, 159, 192, 194; 607/101, 607/102
See application file for complete search history.

(56) References Cited

U.S. PATENT DOCUMENTS

| | | | |
|---|---|---|---|
| 5,057,106 A * | 10/1991 | Kasevich et al. ............ 606/33 |
| 5,196,024 A | 3/1993 | Barath |
| 5,209,799 A | 5/1993 | Vigil |
| 5,224,949 A | 7/1993 | Gomringer et al. |
| 5,226,887 A | 7/1993 | Farr et al. |
| 5,254,089 A | 10/1993 | Wang |
| 5,320,634 A * | 6/1994 | Vigil et al. ................ 606/159 |
| 5,344,401 A | 9/1994 | Radisch et al. |
| 5,366,504 A | 11/1994 | Andersen et al. |
| 5,372,601 A | 12/1994 | Lary |
| 5,405,378 A | 4/1995 | Strecker et al. |
| 5,556,405 A | 9/1996 | Lary |
| 5,578,026 A | 11/1996 | Lavash et al. |
| 5,616,149 A | 4/1997 | Barath |
| 5,624,433 A | 4/1997 | Radisch |
| 5,649,941 A | 7/1997 | Lary |
| 5,653,748 A | 8/1997 | Strecker et al. |
| 5,674,276 A | 10/1997 | Andersen et al. |
| 5,697,944 A | 12/1997 | Lary |
| 5,713,913 A | 2/1998 | Lary et al. |
| 5,746,968 A | 5/1998 | Radisch |
| 5,779,698 A * | 7/1998 | Clayman et al. ............ 606/39 |
| 5,792,158 A | 8/1998 | Lary |
| 5,797,935 A * | 8/1998 | Barath ..................... 606/159 |
| 5,800,450 A | 9/1998 | Lary et al. |
| 5,967,984 A | 10/1999 | Chu et al. |
| 6,009,877 A * | 1/2000 | Edwards .................. 128/898 |
| 6,019,785 A | 2/2000 | Strecker |
| 6,036,689 A * | 3/2000 | Tu et al. .................... 606/41 |

(Continued)

FOREIGN PATENT DOCUMENTS

AU    B-31927/93    1/1993

(Continued)

*Primary Examiner*—Michael Peffley
(74) *Attorney, Agent, or Firm*—Crompton, Seager & Tufte, LLC.

(57) ABSTRACT

Medical systems and related methods are disclosed. In some embodiments, the medical systems include a catheter, an expandable medical device at least partially surrounding a portion of the catheter, a blade attached to the medical device, and an energy transmitter configured so that energy emitted by an energy source can be transmitted to the blade via the energy transmitter.

37 Claims, 5 Drawing Sheets

U.S. PATENT DOCUMENTS

| | | | |
|---|---|---|---|
| 6,091,993 A * | 7/2000 | Bouchier et al. | 607/98 |
| 6,102,908 A * | 8/2000 | Tu et al. | 606/41 |
| 6,117,153 A | 9/2000 | Lary et al. | |
| 6,156,032 A | 12/2000 | Lennox | |
| 6,221,099 B1 | 4/2001 | Andersen et al. | |
| 6,258,108 B1 | 7/2001 | Lary | |
| RE37,315 E | 8/2001 | Lev | |
| 6,296,651 B1 | 10/2001 | Lary et al. | |
| 6,306,151 B1 | 10/2001 | Lary | |
| 6,331,166 B1 * | 12/2001 | Burbank et al. | 600/567 |
| 6,423,058 B1 * | 7/2002 | Edwards et al. | 606/41 |
| 6,425,877 B1 | 7/2002 | Edwards | |
| 6,463,331 B1 | 10/2002 | Edwards | |
| 6,475,213 B1 | 11/2002 | Whayne et al. | |
| 6,482,203 B2 | 11/2002 | Paddock et al. | |
| 6,485,515 B2 | 11/2002 | Strecker | |
| 6,491,710 B2 * | 12/2002 | Satake | 606/191 |
| RE38,091 E | 4/2003 | Strecker | |
| 6,547,788 B1 * | 4/2003 | Maguire et al. | 606/41 |
| 6,589,238 B2 * | 7/2003 | Edwards et al. | 606/41 |
| 6,659,105 B2 * | 12/2003 | Burbank et al. | 128/898 |
| 6,758,847 B2 * | 7/2004 | Maguire | 606/41 |
| 7,153,315 B2 * | 12/2006 | Miller | 606/159 |
| 2003/0069620 A1 | 4/2003 | Li | |
| 2003/0093069 A1 | 5/2003 | Panescu et al. | |
| 2003/0176812 A1 * | 9/2003 | Burbank et al. | 600/567 |

FOREIGN PATENT DOCUMENTS

| | | |
|---|---|---|
| AU | B-27257/92 | 6/1993 |
| AU | B-261119/92 | 7/1993 |
| AU | B-26313/92 | 10/1993 |
| AU | B-28455/92 | 10/1993 |
| AU | B-54906/94 | 11/1994 |
| AU | B-31736/95 | 5/1996 |
| AU | 709938 | 7/1996 |
| AU | 702376 | 3/1998 |
| AU | 714544 | 4/1998 |
| AU | 725324 | 4/1998 |
| AU | 741544 | 2/2000 |
| CA | 2115468 | 1/1996 |
| CA | 2077739 | 5/1996 |
| CA | 2118886 | 12/1998 |
| CA | 2078175 | 5/1999 |
| EP | 0 565 799 | 10/1993 |
| EP | 0 551 707 | 4/1995 |
| EP | 0 721 766 | 7/1996 |
| EP | 0 565 796 | 5/1997 |
| EP | 0 619 986 | 5/1997 |
| EP | 0 554 607 | 11/1997 |
| EP | 0 829 238 | 3/1998 |
| EP | 0 834 287 | 4/1998 |
| EP | 0 623 315 | 6/1999 |
| EP | 0 707 942 | 3/2000 |
| WO | WO 00/69376 | 11/2000 |
| WO | WO 00/72909 | 12/2000 |
| WO | WO 03/041602 | 5/2003 |

* cited by examiner

MEDICAL DEVICE SYSTEMS AND METHODS

TECHNICAL FIELD

This invention relates to medical device systems and related methods.

BACKGROUND

In general, a lumen in a subject (e.g., a human) is a passageway that can transport one or more fluids (e.g., blood, urine, air) from one area of the subject to another area of the subject. Examples of naturally occurring lumens include veins, arteries, bronchi, esophagus, ureter, and urethra. In certain instances, it may be desirable to form a man-made lumen in a subject. For example, when treating scar tissue constriction of a portion of the portal vein (e.g., portal hypertension), a lumen can be formed in the liver to provide a passageway for fluid between the portal vein and the hepatic vein. In some cases, it can be desirable to reinforce such man-made lumens with an endoprosthesis, such as a stent or a stent-graft.

SUMMARY

The invention relates to medical device systems and related methods.

In some embodiments, the systems include a catheter; an expandable medical device that at least partially surrounds a portion of the catheter, a member carried by the medical device, an energy source and an energy transmitter. The member is selected from scoring elements and needles. The energy transmitter is at least partially disposed within the wall of the expandable medical device and configured so that energy emitted by the energy source can be transmitted to the member via the energy transmitter.

In certain embodiments, the systems include a catheter, an expandable medical device that at least partially surrounds a portion of the catheter, a member carried by the medical device, an energy source and an energy transmitter. The member is selected from scoring elements and needles. The energy transmitter is at least partially disposed within the wall of the expandable medical device and configured so that, when the expandable medical device is disposed within a subject adjacent tissue, energy emitted by the energy source can be transmitted to the tissue via the energy transmitter.

In some embodiments, the methods include inserting such a system into a lumen in an organ of a subject.

In certain embodiments, the methods include engaging a scoring element with a wall of a lumen in the organ, and, after engaging the scoring element with the wall of the lumen in the organ, heating the organ. The scoring element is carried by an expandable medical device Embodiments can provide one or more of the following advantages.

In some embodiments, a system can be used to reinforce a lumen in an organ in a subject so that, after treatment, the lumen is sufficiently reinforced without the presence of a reinforcing element, such as an endoprosthesis. The organ can be, for example, the liver, the kidney, the prostate, the heart, the gallbladder, the pancreas, the esophagus, the lungs and bronchi, and/or the reproductive organs (e.g., fallopian tubes, vas defrens).

In certain embodiments, a method can involve using a relatively uniform dispersion of energy to reinforce a lumen in an organ in a subject. This can allow for relatively uniform, reproducible and/or predictable reinforcement of the lumen.

In some embodiments, a system can include a bipolar energy design. This can, for example, allow for improved control over a treatment area.

In certain embodiments, a system can be designed to have one or more energy transmitters (e.g., wires) protected by the catheter and the expandable medical device so that the energy transmitters do not come into contact with a lumen in a subject during treatment of the subject. This can reduce the trauma associated with introducing the system into the lumen, and/or reduce damage to the energy transmitters associated with introducing the system into the lumen.

Other features and advantages will be apparent from the description, drawings and claims.

DESCRIPTION OF DRAWINGS

Like reference symbols in the various drawings indicate like elements.

DETAILED DESCRIPTION

Figure 1A:
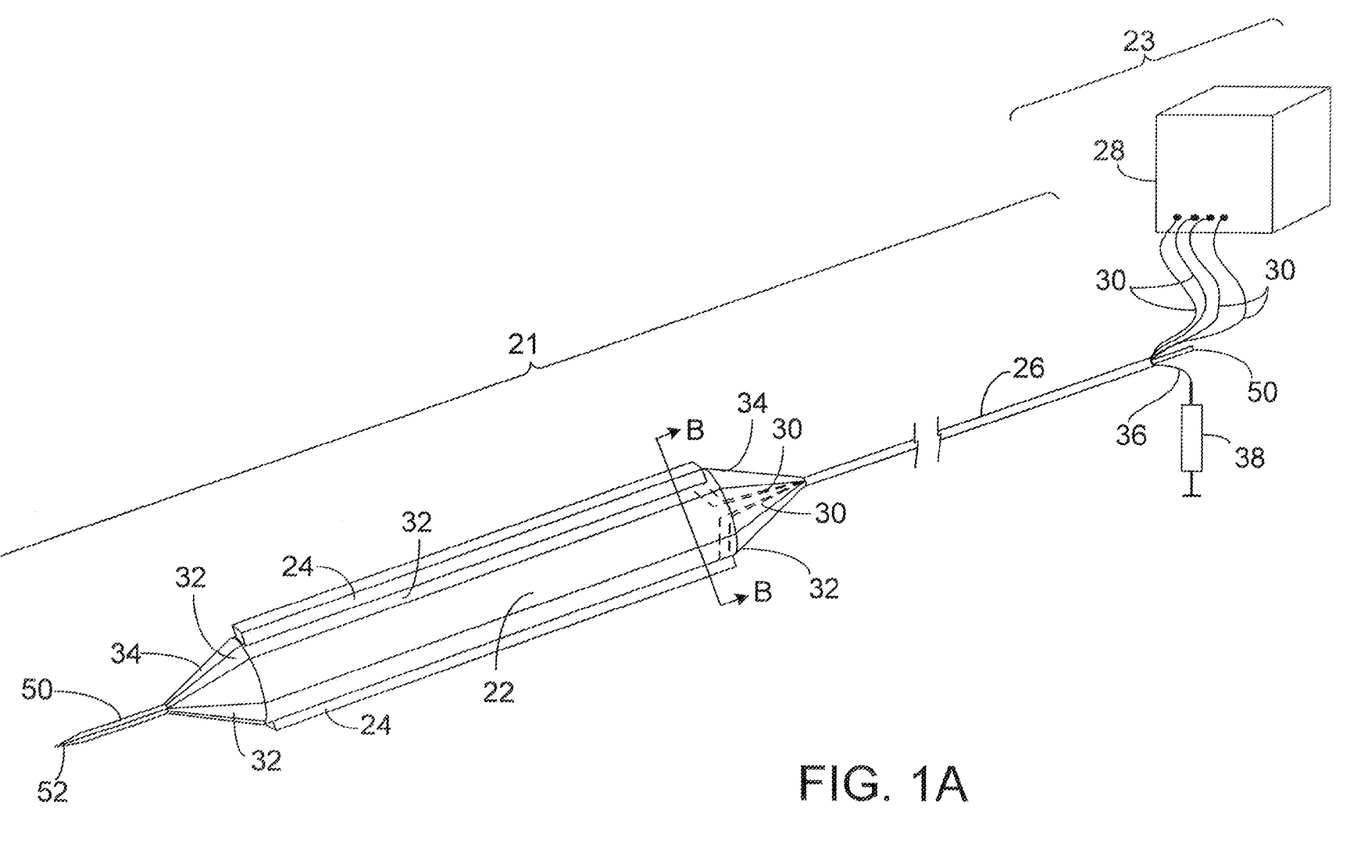
FIG. 1A is a perspective view of an embodiment of a medical device system.
Figure 1B:
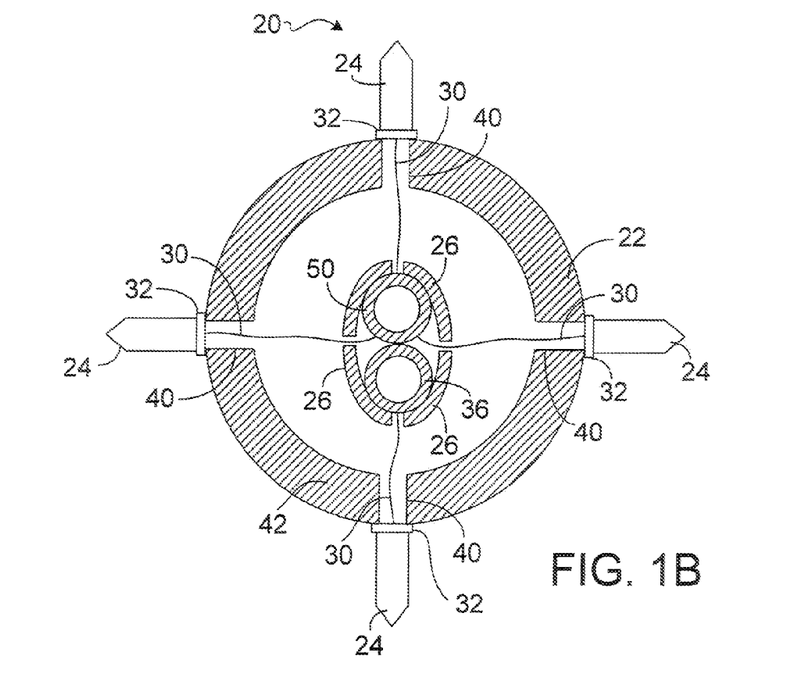
FIG. 1B is a cross-sectional view of the medical device system taken along line B-B in FIG. 1A.

FIGS. 1A and 1B show a medical device system 20 that can be used to form, expand and reinforce a lumen in an organ of a subject (e.g., a human liver). System 20 includes an expandable balloon portion 21 and an energy source portion 23.

Expandable balloon portion 21 includes an expandable balloon 22 and scoring elements 24 secured to expandable balloon 22 via conductive strips 32. Conductive strips 32 may be adhered to balloon 22 by, for example, an adhesive (e.g., a polyurethane-based adhesive) or attached by melting the balloon polymer or another polymer to the balloon. Transition cones 34 (e.g., formed of a biocompatible stiff material, such as plastic) are disposed on distal and proximal portions of balloon 22. Portion 21 also includes a catheter 26 extending from a region proximal of balloon 22 and through an interior region of balloon 22. Catheter 26 houses an inflation channel 36 that is in fluid communication with an inflation device (e.g., injection syringe) 38. Catheter 26 also houses a removable puncture system 50 that extends from a proximal end of catheter 26 to a sharp tip 52.

As referred to herein, a scoring element is a member (e.g., a blade, a needle) that is capable of scoring and/or cutting into tissue, a stenosis or the like. Scoring elements 24 are RF conductive and act as antennae to deliver RF energy. As shown in FIGS. 1A and 1B, in certain embodiments four scoring elements 22 are equally spaced about the circumference of balloon 22 to equally distribute energy to the surrounding tissue. Optionally, balloon 22 can include fewer than four (e.g., one, two, three) scoring elements and/or more than four (e.g., five, six, seven, eight, nine, 10) scoring elements).

Energy source portion 23 includes a radio-frequency ("RF") energy source 28 (e.g., a Radiotherapeutics RF generator available from Boston Scientific Corp., Natick, Mass.) and wires 30. Wires 30 extend from energy source 28, through catheter 26, through channels 40 in a wall 42 of balloon 22, and to conductive strips 32, which form a fluid-tight seal with balloon 22. With this arrangement, RF energy can be transmitted from energy source 28 to scoring elements 24. Positioning wires 30 within catheter 26 and wall 42 of balloon 22 reduces irritation and/or trauma to the subject's body associated with the use of system 20 (see discussion below). Additionally or alternatively, positioning wires 30 within catheter 26 and wall 42 of balloon 22 can reduce damage (e.g., undesired bending, undesired kinking) to wires 30 during use of system 20 (see discussion below).

During use of system 20, tip 52 is used to pierce tissue in a subject's body, thereby forming a lumen in the body of the subject. For example, in some embodiments, tip 52 is used to pierce tissue to form a lumen that passes through the liver and connects the hepatic vein to the portal vein. While present within the lumen, balloon 22 is expanded by injecting a liquid (e.g., saline, nitrogen, water) from inflation device 38 into inflation channel 36. As balloon 22 expands, scoring elements 24 contact the walls of the lumen tissue and can begin to score (generally weaken by, for example, cutting and/or piercing) the lumen walls. At the same time, RF energy is transmitted from energy source 28 to scoring elements 24. Scoring elements 24 radiate the energy (e.g., in the form of heat) to the lumen wall. The heat ablates and/or cauterizes tissue in the lumen wall, which hardens the tissue (e.g., by denaturing the tissue) and reinforces the lumen wall (e.g., increases the hoop strength of the lumen wall), and system 20 is then removed from the subject.

In general, the temperature to which the lumen wall is heated by scoring elements 24 and the amount of time that lumen wall is heated are selected to effect a change in the tissue (e.g., via cauterization of the tissue) to result in desirable reinforcement without undesirable tissue damage. In certain embodiments, the lumen wall is heated to a temperature of at least about 38° C. (e.g., at least about 45° C., at least about 50° C.) and/or at most about 95° C. (e.g., at most about 85° C., at most about 70° C.) for an amount of time sufficient to obtain desired reinforcement without undesirable tissue damage. As an example, in certain embodiments, the lumen wall is heated to a temperature of from about 75° C. to about 90° C. for a time period of from about five seconds to about 15 seconds so that water within the tissue is expelled, and the tissue retracts in response to the treatment. As another example, in some embodiments, the lumen wall is heated to a temperature of about 40° C. for a time period of from about five minutes to about 15 minutes so that the tissue initially swells in response to the heat treatment, and then in time (e.g., after 10 hours, after 15 hours, after 20 hours, after 25 hours, after 30 hours, after 35 hours, after 40 hours) retracts.

In general, the diameter of the lumen wall after treatment depends upon the particular lumen formed. For example, in certain embodiments in which the lumen is used to form a passageway between the hepatic vein to the portal vein, the lumen wall can be several millimeters in diameter (e.g., about six millimeters in diameter, about seven millimeters in diameter, about eight millimeters in diameter, about nine millimeters in diameter, about 10 millimeters in diameter, about 10.5 millimeters in diameter, 11 millimeters in diameter, 11.5 millimeters in diameter, 12 millimeters in diameter, and 12.5 millimeters in diameter).

Figure 2A:
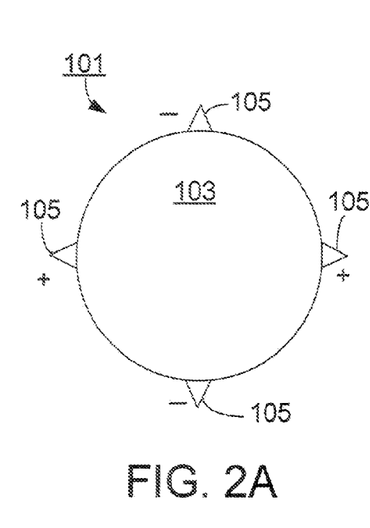
FIGS. 2A-2I are a cross-sectional views of embodiments of bipolar systems.
Figure 2B:
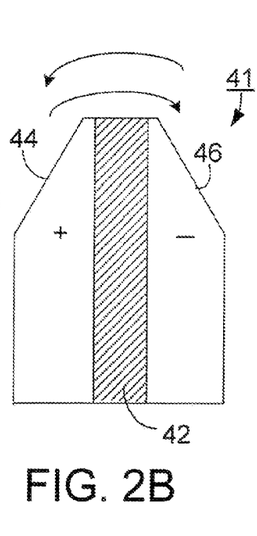
Figure 2C:
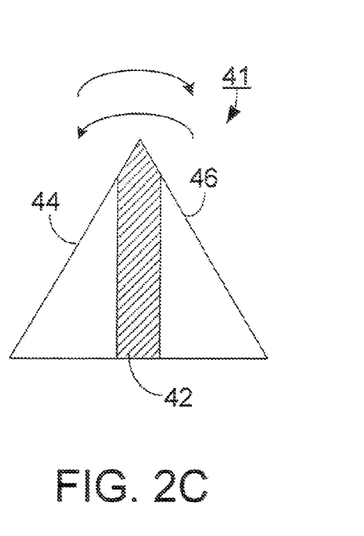
Figure 2D:
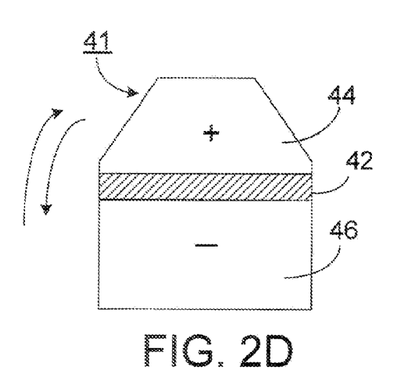
Figure 2E:
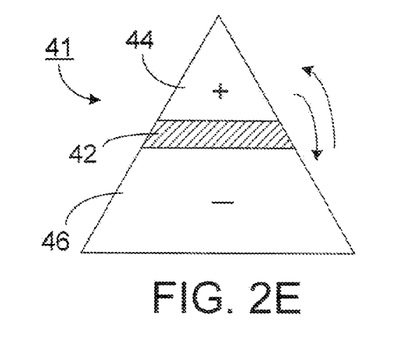
Figure 2F:
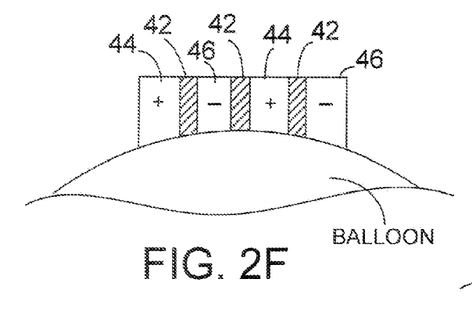
Figure 2G:
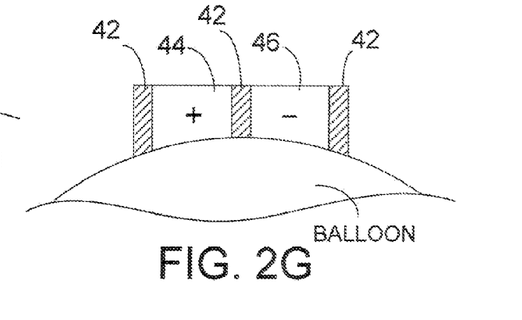
Figure 2H:
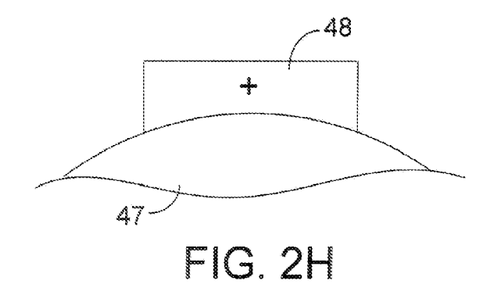
Figure 2I:
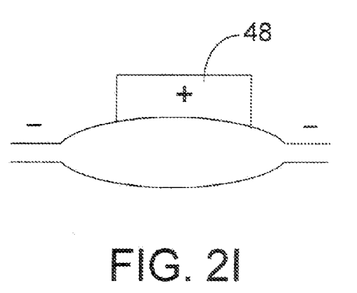

In general, wires 30 can be configured to transmit RF energy in a monopolar design or a bipolar design. In embodiments having a monopolar design, one pole is used, and the grounding plate is typically outside the subject (e.g., under the subject's back or buttocks). In embodiments having a bipolar design, each scoring element can act as an antenna transmitting energy to the tissue in contact with the scoring element. In embodiments having a bipolar design, the scoring elements are typically configured to form alternating positively charged poles and negatively charged poles so that energy radiates outwardly from the scoring elements and into the tissue. In general, an insulating material is positioned between oppositely charged scoring elements in a bipolar design. FIG. 2A is an illustration of a bipolar system 101 including a balloon 103 and scoring elements 105, in which alternating scoring elements 105 are oppositely charged. FIG. 2B shows an embodiment of a bipolar design including a scoring element 41 that can include an insulated bushing 42 positioned between conductive regions 44 and 46 to create a potential difference across scoring element 41 so that a positively charged pole is formed at region 44 and a negatively charged pole is formed at region 46. This creates a RF energy field that extends beyond scoring element 41 and supplies energy to the surrounding tissue within the field. In FIG. 2B, the bi-pole is along the vertical length of scoring element 41. FIG. 2C is similar to FIG. 2B, except that scoring element 41 has a different shape. FIGS. 2D and 2E are embodiments of bipolar scoring elements in which the bi-pole is along the horizontal length of scoring element 41. FIGS. 2F and 2G are illustrations of embodiments in which the bi-pole along the length of scoring element 41. In FIG. 2H and 2I, the bi-pole is between the balloon 47 and scoring element 48. In such embodiments, either the balloon or the catheter may have sufficient conductivity to act as a pole. This can be achieved, for example, by using conductive polymers in the balloon or catheter construction. Alternatively, conductive (e.g., metal or alloy) coatings can be present on the balloon or catheter, conductive (e.g., metal or alloy) wires can be embedded in the balloon or catheter, or a conductive material can be applied (e.g., in the form of an ink, a paint, a polymer, a metal or an alloy) to the catheter or balloon.

In some embodiments, a scoring element can extend at least about 10% (e.g., at least about 20%, at least about 30%, at least about 40%, at least about 50%, at least about 60%, at least about 70%, at least about 80%, at least about 90%) of the medical balloon's longitudinal length.

In general, a scoring element for use with an RF energy source is formed of a material that is electrically conductive, preferably compatible with magnetic resonance imaging (e.g., having a sufficient contrast to noise ratio so that a medical professional can identify an edge of the one or more scoring elements in a MRI scan) and/or thermally conductive. Examples of materials from which a scoring element can be formed include graphitic carbon, stainless steel, inconel and gold.

A medical balloon can generally have any of a variety of shapes or sizes. In certain embodiments, the medical balloon can be a coronary balloon, an aortic balloon, a peripheral balloon, a reperfusion balloon, an endoscopy balloon, a gastrointestinal balloon, a urological balloon, a neurological balloon, a genitourinary balloon or a pulmonary balloon. In some embodiments, the medical balloon has a diameter of at least 1.5 millimeters (e.g., at least about two millimeters, at least about three millimeters, at least about four millimeters, at least about five millimeters, at least about six millimeters) when inflated. As an example, the medical balloon can be a peripheral balloon having a diameter of at least about three millimeters (e.g., at least about five millimeters, at least about seven millimeters, at least about nine millimeters, at least about 12 millimeters) when inflated. As another example, the medical balloon can be a urological balloon having a diameter at least about four millimeters (e.g., at least about 10 millimeters, at least about 20 millimeters, at least about 30 millimeters, at least about 40 millimeters) when inflated. As a further example, the medical balloon can be a neurological balloon having a diameter at least about 1.5 millimeters (e.g., at least about two millimeters, at least about three millimeters, at least about four millimeters, at least about five millimeters).

While certain embodiments have been described, other embodiments are also possible.

As an example, while systems using RF energy sources have been described, in some embodiments one or more different energy sources may be used. Examples of such energy sources include microwave energy sources, ultrasonic energy sources, lasers, resistance heating and heat conducting. In general, the scoring elements are formed of materials that transmit the energy created by the energy source used. As an example, if an ultrasound energy source is used, then the scoring element(s) are formed of a material that transmits ultrasound energy, such as ceramics. As another example, if a microwave energy source is used, then the scoring element(s) are formed of a material that transmits microwave energy, such as discussed above with respect to RF energy. As an example, if a laser is used, then the scoring element(s) are formed of a material that transmits light of the wavelength emitted by the laser, such as optical quality materials (e.g., optical quality glass, optical quality polymers).

As another example, while a medical device system has been described as being using to treat portal hypertension, the medical device system can be used to treat other passageways in a patient's body. For example, in certain embodiments, a medical device system can be used to treat blockages in arteries (e.g., coronary, peripheral), veins, the urinary tract, the gastrointestinal tract, the esophagus, the biliary duct, the pancreas, the lungs and bronchi, the reproductive organs (e.g., fallopian tubes, vas defrens).

As an additional example, while embodiments have been described in which a reinforcing element is not used in the process, in some embodiments a reinforcing element (e.g., a stent, a stent-graft) can be used to reinforce the lumen. In such embodiments, the reinforcing element is typically disposed within the lumen subsequent to formation of the lumen. The reinforcing element can assist in maintained desired reinforcement.

As another example, in some embodiments, the conduction system can be embedded within the balloon wall or may be captured between two disconnected balloon membranes.

As an additional example, a channel balloon can be used, where the leads/wires can extend through the channels (e.g., instead of through the inflation lumen). Such balloons are disclosed, for example, in U.S. Pat. Nos. 5,403,820 and 5,860,954, which are hereby incorporated by reference.

As a further example, while medical device systems having an expandable balloon have been described, in certain embodiments a different expandable medical device can be used (e.g., an expandable stent, an expandable cage, a device including a malecot).

Figure 3A:
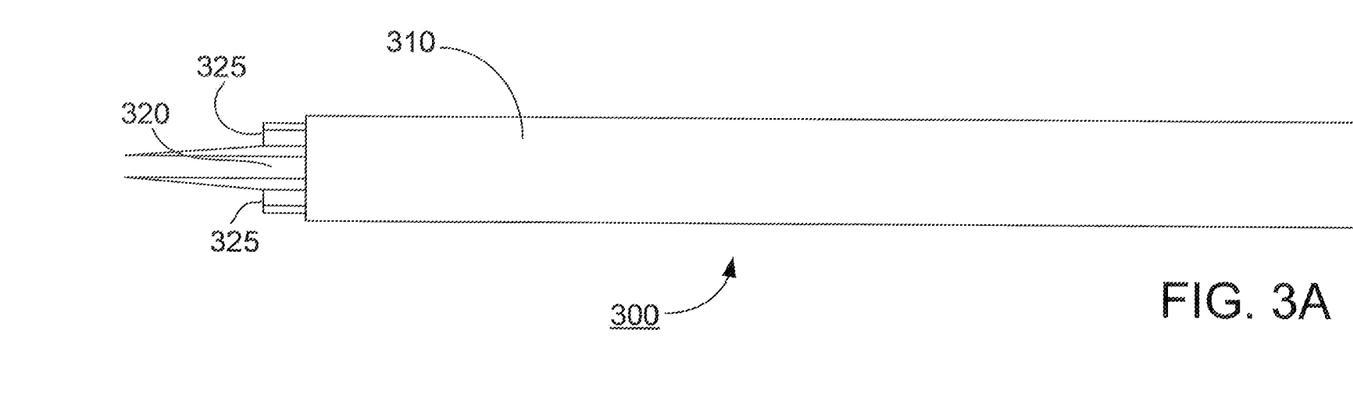
FIG. 3A is a side view of an embodiment of a medical device system within a sheath that maintains an expandable medical device in a collapsed state.
Figure 3B:
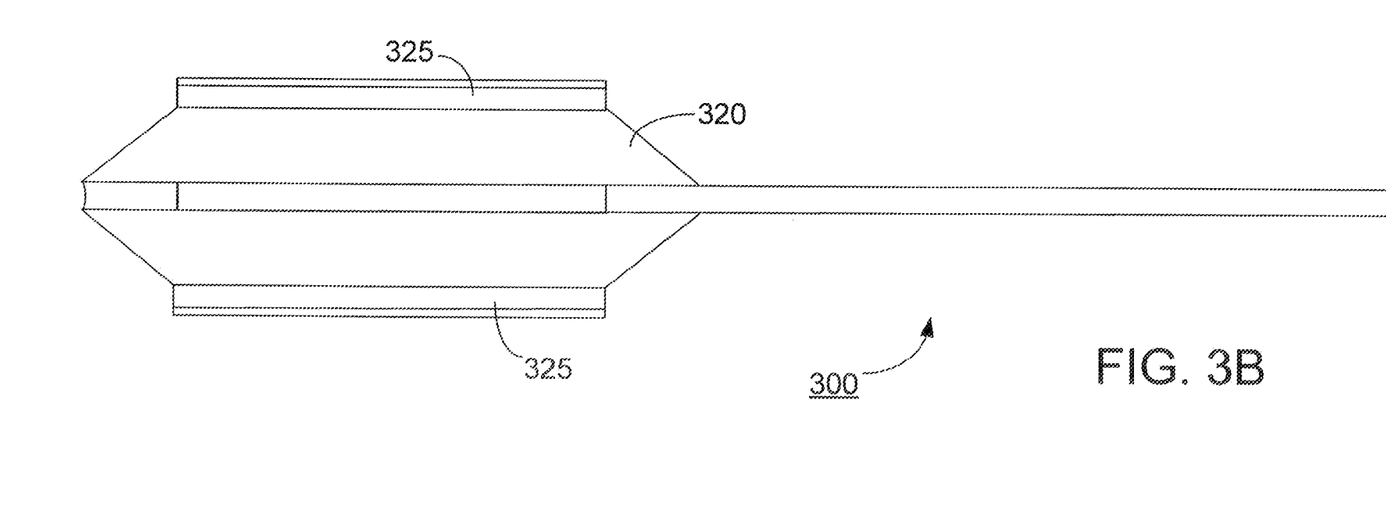
FIG. 3B is a side view of the medical device system of FIG. 3A after the sheath has been removed.
Figure 4A:
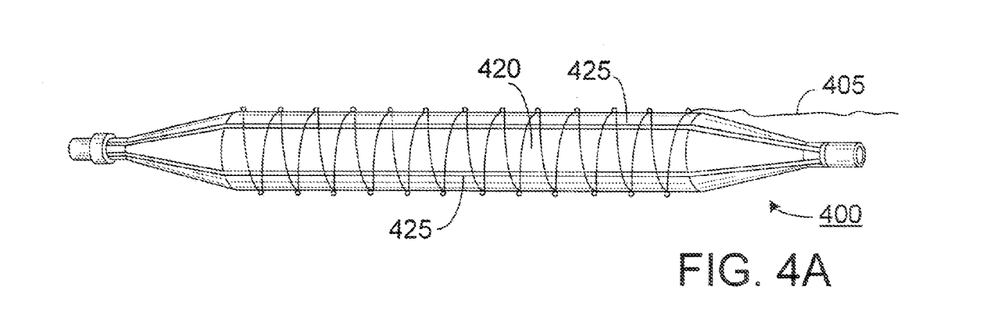
FIG. 4A is a side view of an embodiment of a medical device system that includes a pull string that collapses an expandable medical device when pulled.
Figure 4B:
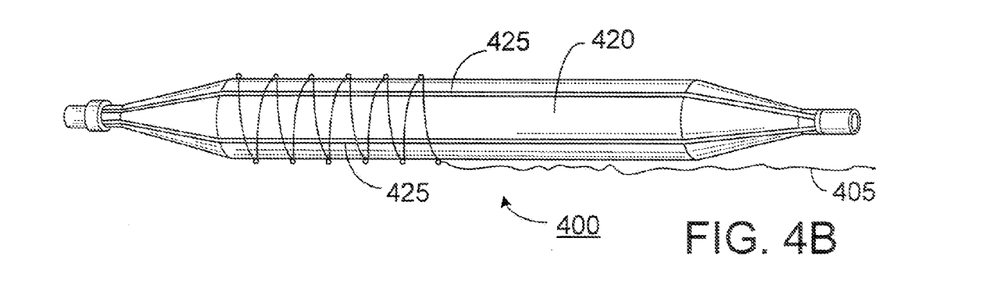
FIG. 4B is a side view of the medical device system of FIG. 4A after the pull string has been partially released.
Figure 4C:
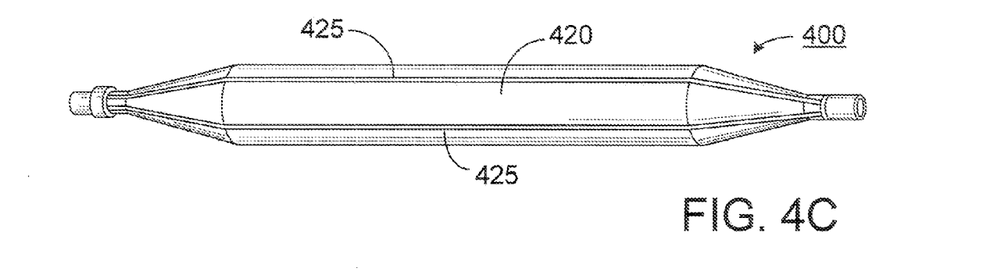
FIG. 4C is a side view of the medical device system of FIG. 4A after the pull string has been released but the medical device has not been expanded.
Figure 4D:
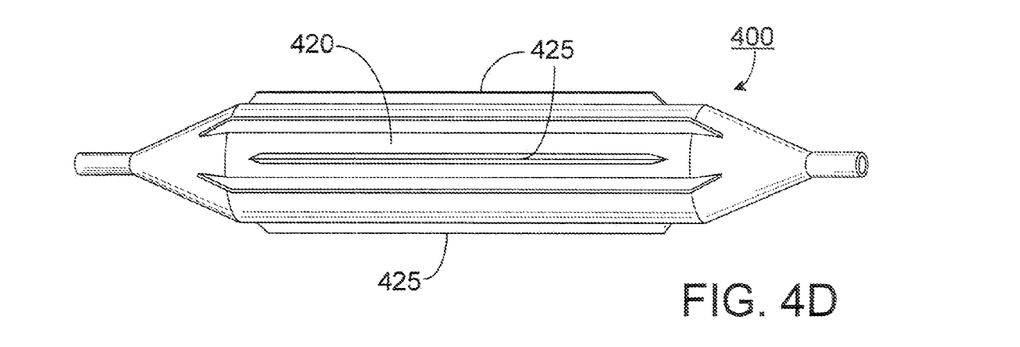
FIG. 4D is a side view of the medical device system of FIG. 4A after the pull string has been partially released and the medical device has been expanded.

As shown in FIGS. 3A and 3B, in certain embodiments, a medical device system 300 can include a sheath 310 that retains an expandable medical device 320 in an unexpanded state (FIG. 3A) until system 300 is positioned within the lumen. Once system 300 is positioned within the lumen, sheath 310 can be retracted so that expandable medical device 320 expands and scoring elements 325 contact the lumen wall (FIG. 3B). As shown in FIGS. 4A-4D, in some embodiments, a medical device system 400 includes a pull string 405 that is attached to an expandable medical device 420. Pull string 405 collapses expandable device 420 to an unexpanded state when pulled towards a proximal end of medical device system 400 (FIGS. 4A and 4B). Upon release of pull string 405, expandable medical device 420 can be expanded and scoring elements 425 contact the lumen wall (FIGS. 4C and 4D). Medical device systems are disclosed, for example, in U.S. Pat. Nos. 5,366,504; 5,405,378; 5,578,026; 5,653,748; 5,674,276; 6,019,785; 6,221,099; 6,485,515; and U.S. Pat. No. RE38,091, which are all hereby incorporated by reference.

Other embodiments are in the claims.

What is claimed is:

1. A system, comprising:
   a catheter;
   an expandable medical device at least partially surrounding a portion of the catheter, the expandable medical device having a wall that at least partially defines an expandable region of the expandable medical device, the wall having an inner surface and an outer surface;
   first and second blades carried by the medical device and extending in a direction along a longitudinal length of the expandable medical device, wherein each blade includes a first portion having a positively charged pole and a second portion having a negatively charged pole;
   an energy source; and
   an energy transmitter extending through the wall in the expandable region of the expandable medical device such that the energy transmitter passes from the inner surface of the wall to the outer surface of the wall, the energy transmitter configured so that energy emitted by the energy source can be transmitted to at least one of the blades via the energy transmitter.

2. The system of claim 1, wherein the energy transmitter contacts the first blade.

3. The system of claim 1, wherein the energy transmitter comprises at least one wire.

4. The system of claim 1, wherein each of the blades are attached to the expandable medical device via a conductive strip.

5. The system of claim 1, wherein each of the blades extends along at least 10% of a longitudinal length of the expandable medical device.

6. The system of claim 1, wherein the expandable medical device is a medical balloon.

7. The system of claim 6, wherein the medical balloon is selected from the group consisting of coronary balloons, aortic balloons, peripheral balloons, reperfusion balloons, endoscopy balloons, urology balloons, neurology balloons, genitourinary balloons and pulmonary balloons.

8. The system of claim 1, wherein the expandable medical device is selected from the group consisting of stents, expandable cages and malecots.

9. The system of claim 1, further comprising a puncture system comprising a sharp tip, the puncture system being configured such that the sharp tip can extend distal to the expandable medical device.

10. A system, comprising:
a catheter;
an expandable medical device at least partially surrounding a portion of the catheter, the expandable medical device having a wall that at least partially defines an expandable region of the expandable medical device, the wall having an inner surface and an outer surface;
a blade having a surface attached to the medical device and extending in a direction along a longitudinal length of the expandable medical device, wherein the blade includes a first portion having a positively charged pole and a second portion having a negatively charged pole;
an energy source; and
an energy transmitter in contact with the surface of the blade and extending through the wall in the expandable region of the expandable medical device such that the energy transmitter passes from the inner surface of the wall to the outer surface of the wall, the energy transmitter being configured so that energy emitted by the energy source can be transmitted to the blade via the energy transmitter.

11. The system of claim 10, further comprising a puncture system comprising a sharp tip, the puncture system being configured such that the sharp tip can extend distal to the expandable medical device.

12. A method comprising:
forming a man-made lumen in an organ tissue of a subject by piercing the organ tissue; and then
engaging a blade with a wall of the man-made lumen in the organ tissue and simultaneously heating the organ tissue, the blade being carried by an expandable balloon and extending in a direction along a longitudinal length of the expandable balloon.

13. The method of claim 12, wherein the expandable balloon at least partially surrounds a catheter.

14. The method of claim 12, wherein the organ tissue is heated by passing energy from an energy source to the blade via an energy transmitter.

15. The method of claim 12, wherein the method increases a hoop stress of the wall of the man-made lumen in the organ tissue.

16. The method of claim 12, wherein the method increases an inner diameter of the man-made lumen in the organ tissue.

17. The method of claim 12, wherein the organ tissue is heated to a temperature of at least about 38° C.

18. The method of claim 17, wherein the temperature to which the organ tissue is heated is at most about 95° C.

19. The method of claim 12, wherein the organ tissue is pierced with a sharp tip of a puncture system extending distal to the expandable balloon.

20. A method of treating a subject, comprising:
inserting a system into a lumen in an organ of the subject, the system comprising:
a catheter;
an expandable medical device at least partially surrounding a portion of the catheter, the expandable medical device having a wall that at least partially defines an expandable region of the expandable medical device, the wall having an inner surface and an outer surface;
first and second blades carried by the medical device and extending in a direction along a longitudinal length of the expandable medical device, wherein each blade includes a first portion having a positively charged pole and a second portion having a negatively charged pole;
an energy source; and
an energy transmitter extending through the wall in the expandable region of the expandable medical device such that the energy transmitter passes from the inner surface of the wall to the outer surface of the wall, the energy transmitter configured so that energy emitted by the energy source can be transmitted to at least one of the blades via the energy transmitter.

21. The method of claim 20, further comprising expanding the expandable medical device so that at least one of the blades engages a wall of the lumen in the organ.

22. The method of claim 21, wherein at least one of the blades cuts into a portion of the organ.

23. The method of claim 21, further comprising passing energy from the energy source to at least one of the blades via the energy transmitter and passing energy from at least one of the blades to the organ.

24. The method of claim 23, wherein the method increases a hoop stress of a wall of the lumen.

25. The method of claim 23, wherein the method increases an inner diameter of the lumen in the organ.

26. The method of claim 23, wherein the organ is heated to a temperature of at least about 38° C.

27. The method of claim 26, wherein the temperature to which the organ is heated is at most about 95° C.

28. The method of claim 20, further comprising simultaneously expanding the expandable medical device and passing energy from the energy source to at least one of the blades via the energy transmitter and passing energy from at least one of the blades to the organ.

29. The method of claim 20, wherein the organ tissue is pierced with a sharp tip of a puncture system extending distal to the expandable balloon.

30. A method of treating an organ or subject, comprising:
inserting a system into a lumen in the organ of the subject, the system comprising:
a catheter;
an expandable medical device at least partially surrounding a portion of the catheter, the expandable medical device having a wall that at least partially defines an expandable region of the expandable medical device, the wall having an inner surface and an outer surface;
a blade having a surface attached to the medical device and extending in a direction along a longitudinal length of the expandable medical device, wherein the blade includes a first portion having a positively charged pole and a second portion having a negatively charged pole;
an energy source; and
an energy transmitter in contact with the surface of the blade and extending through the wall in the expandable region of the expandable medical device such that the energy transmitter passes from the inner surface of the wall to the outer surface of the wall, the energy transmitter being configured so that energy emitted by the energy source can be transmitted to the blade via the energy transmitter.

31. The method of claim 30, wherein the organ tissue is pierced with a sharp tip of a puncture system extending distal to the expandable balloon.

32. A system, comprising:
a catheter;
an expandable medical device at least partially surrounding a portion of the catheter, the expandable medical device having a wall that at least partially defines an expandable region of the expandable medical device, the wall having an inner surface and an outer surface;

a blade carried by the medical device and extending in a direction along a longitudinal length of the expandable medical device, wherein the blade includes a first portion having a positively charged pole and a second portion having a negatively charged pole;

an energy source; and an energy transmitter electrically coupled to the blade and configured so that, when the expandable medical device is disposed within a subject adjacent tissue, energy emitted by the energy source can be transmitted to the tissue via the energy transmitter.

33. The system of claim 32, wherein the energy is transmitted from the energy transmitter to the tissue via the blade.

34. The system of claim 32, further comprising a puncture system comprising a sharp tip, the puncture system being configured such that the sharp tip can extend distal to the expandable medical device.

35. A method comprising:

forming a man-made lumen in organ tissue of a subject by piercing the organ tissue;

then engaging a blade with a wall of the man-made lumen in the organ tissue; and after engaging the blade with the wall of the man-made lumen in the organ tissue, heating the organ tissue, wherein the blade is carried by an expandable balloon and extends in a direction along a longitudinal length of the expandable balloon.

36. The method of claim 35, wherein the blade cuts the wall of the man-made lumen in the organ tissue before being heated.

37. The method of claim 35, wherein the organ tissue is pierced with a sharp tip of a puncture system extending distal to the expandable balloon.

* * * * *